United States Patent [19]
Balbierz et al.

[11] Patent Number: 5,599,291
[45] Date of Patent: Feb. 4, 1997

[54] SOFTENING EXPANDING URETERAL STENT

[75] Inventors: Daniel J. Balbierz, San Carlos; Jack M. Walker, Portola Valley; Joseph R. Thomas, San Carlos; Robert S. Bley, Menlo Park, all of Calif.

[73] Assignee: Menlo Care, Inc., Menlo Park, Calif.

[21] Appl. No.: 274

[22] Filed: Jan. 4, 1993

[51] Int. Cl.$^6$ .................................................. A61M 37/00
[52] U.S. Cl. ........................ 604/8; 604/264; 604/280
[58] Field of Search ........................... 604/8, 9, 10, 175, 604/264, 283, 93, 95, 282, 281, 280

[56] References Cited

U.S. PATENT DOCUMENTS

| | | | |
|---|---|---|---|
| 4,337,010 | 3/1983 | Fydelor et al. | |
| 4,762,128 | 8/1988 | Rosenbluth | |
| 4,813,925 | 3/1989 | Anderson, Jr. et al. | |
| 4,820,262 | 4/1989 | Finney | 604/8 |
| 4,878,906 | 11/1989 | Lindemann et al. | |
| 4,893,623 | 1/1990 | Rosenbluth | |
| 5,085,629 | 2/1992 | Goldberg et al. | |
| 5,129,910 | 7/1992 | Phan et al. | |
| 5,139,480 | 8/1992 | Hickle et al. | 604/8 |
| 5,169,720 | 12/1992 | Blaatz et al. | 604/8 X |
| 5,221,253 | 6/1993 | Coll | 604/8 |
| 5,234,457 | 8/1993 | Anderson | |

FOREIGN PATENT DOCUMENTS

| | | |
|---|---|---|
| 2641692 | 7/1990 | France |
| 2-144074 | 6/1990 | Japan |
| 2-144073 | 6/1990 | Japan |
| 3-21262 | 1/1991 | Japan |
| PCTWO86/039 | 7/1986 | WIPO |

OTHER PUBLICATIONS

Ureteral Stents Materials—Hal K. Mardis, M.D. and R. Michael Kroeger, M.D.—Urologic Clinics of North America—vol. 15, No. 3, Aug. 1988.

Experimental Embolization of Hypan–R Into Rabbit Kidneys—Daniel P. Link—Abstract from Sixteenth Anual Meeting of the Society of Cardiovascular and Interventional Radiology—Interventional Radiology 1991—Feb. 16–21, 1991.

Hypan–R, A Promising New Embolic Agent—Possibilities & Capabilities—Dr. Daniel P. Link, Dr. Blashka, Dr. Tesluk and Dr. Gu—Abstract from Meeting of Cardiovascular and Interventional Radiological Society of Europe—Society of Cardiovascular and Interventional Radiology—Joint Meeting, Oslo, May 13–16, 1991.

Publication by Kingston—Date Unknown.

Evaluation of Polymeric Materials For Endourologic Devices—Emerging Importance of Hydrogels—Hal K.Mardis, M.D.—Seminars in Interventional Radiology, vol. 4, No. 1, Mar. 1987.

New Type of Hydrogel for Controlled Drug Delivery—Vladimir A. Stoy, Ph.D.—Kingston Technologies, Inc.—Journal of Biomaterials Applications, vol. 3, Apr. 1989.

Experimental Study of Hydrophilic Plastics for Urological Use—J. W. A. Ramsay, R. A. Miller, P. R. Crocker, B. J. Ringrose, S. Jones, D. A. Levison—British Journal of Urology (1986), vol. 58, pp. 70–74.

Kingston Technologies—A Brief Description of the Company, Its Products and Technology—Jun., 1989.

Hydrogels: Specialty Plastics For Biomedical, Pharmaceutical And Industrial Applications—Vladimir A. Stoy, Ph.D., Charles K. Kliment, Ph.D.—The Colony Square Hotel, Atlanta, Georgia—Apr. 19–20, 1990.

*Primary Examiner*—Sam Rimell
*Attorney, Agent, or Firm*—Fliesler, Dubb, Meyer & Lovejoy

[57] ABSTRACT

A ureteral stent comprising an elongated member having a proximal end portion and a distal end portion joined by a body portion. The elongated member has an initial outer diameter. A retention construction serves for retaining the member within the ureter. The member is formulated of a physiologically acceptable polymer capable of hydrating and expanding from the initial member outer diameter to form a final member outer diameter. The stent can assume differing shapes and can exhibit different degrees of softening at different places along its length.

40 Claims, 6 Drawing Sheets

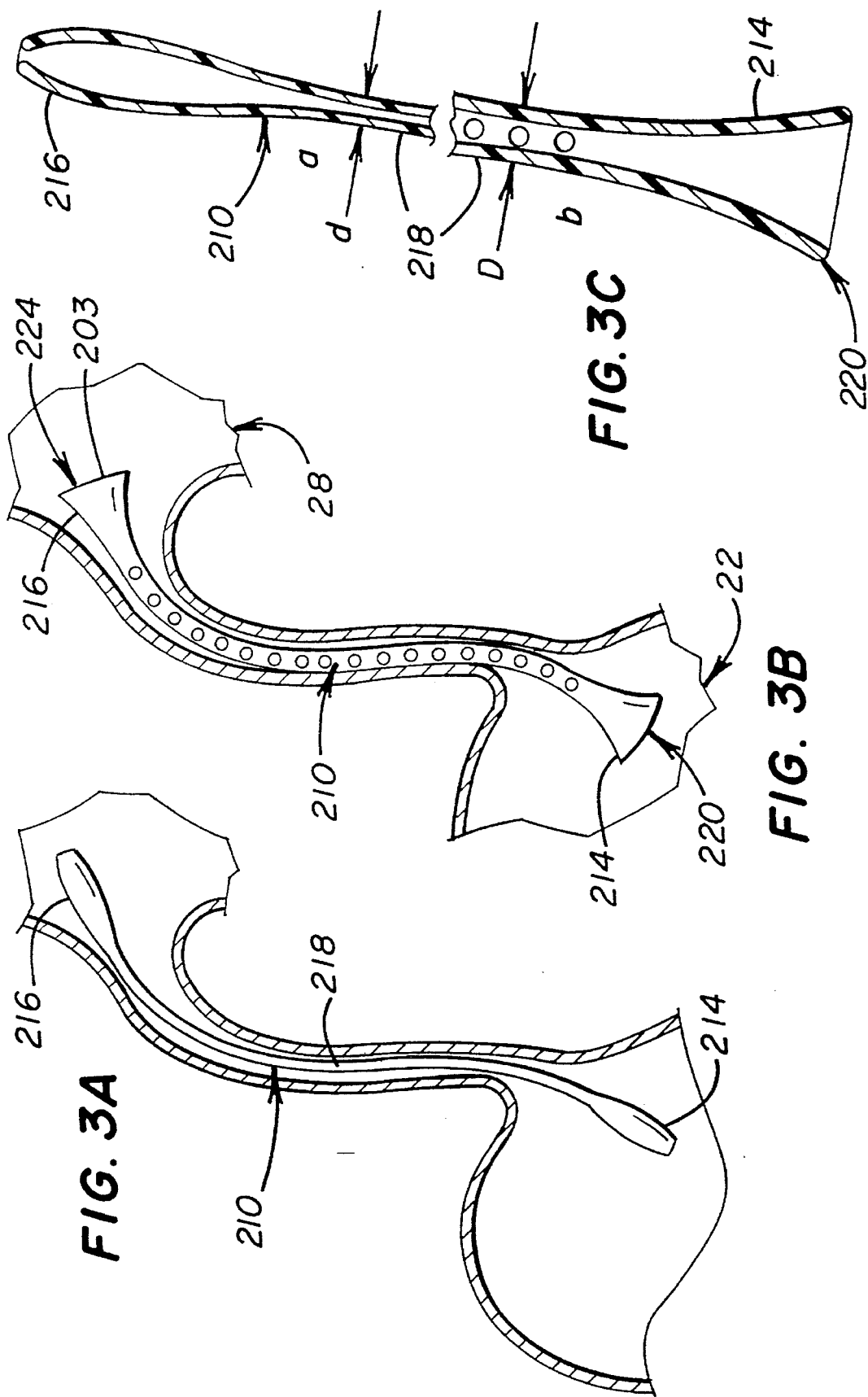

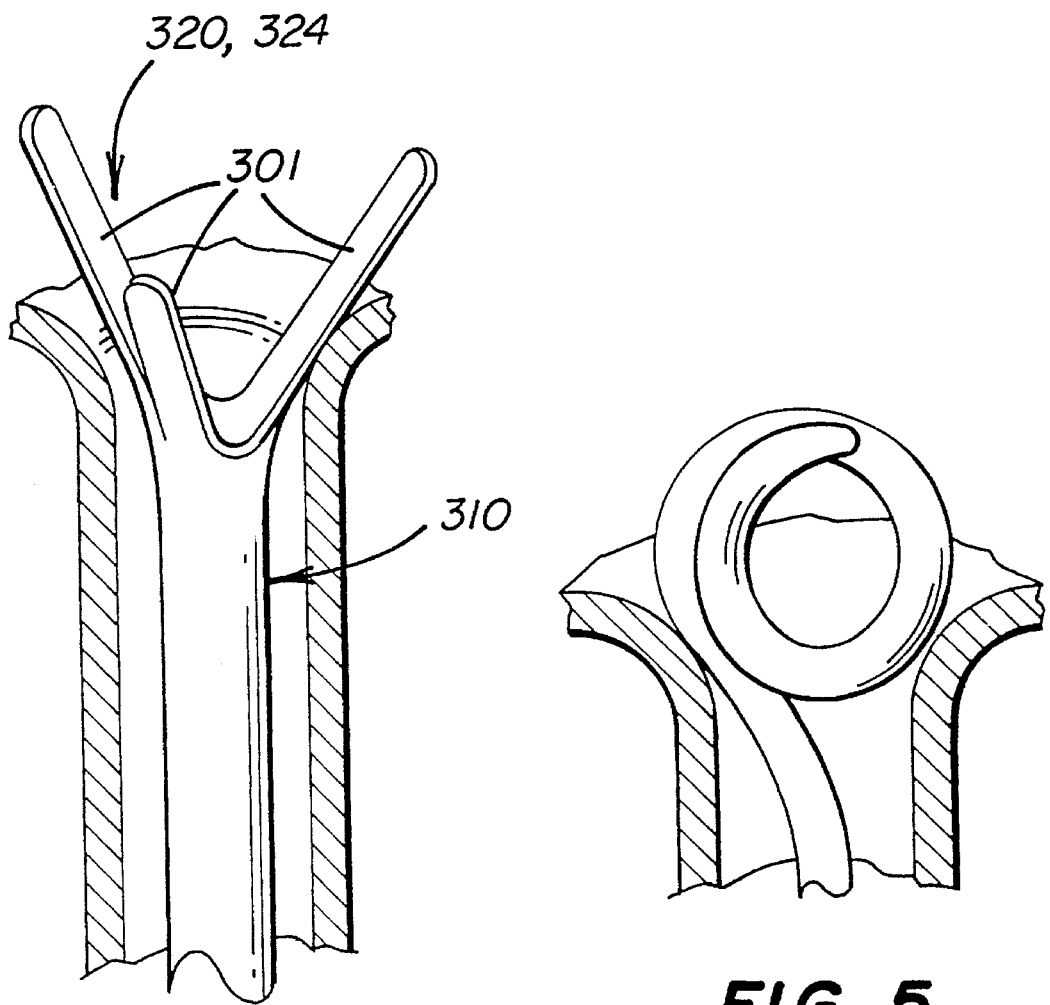
FIG. 4
FIG. 5
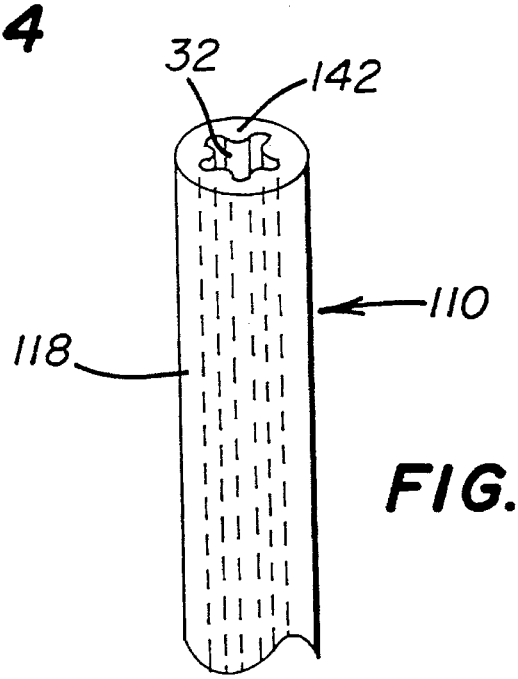
FIG. 10

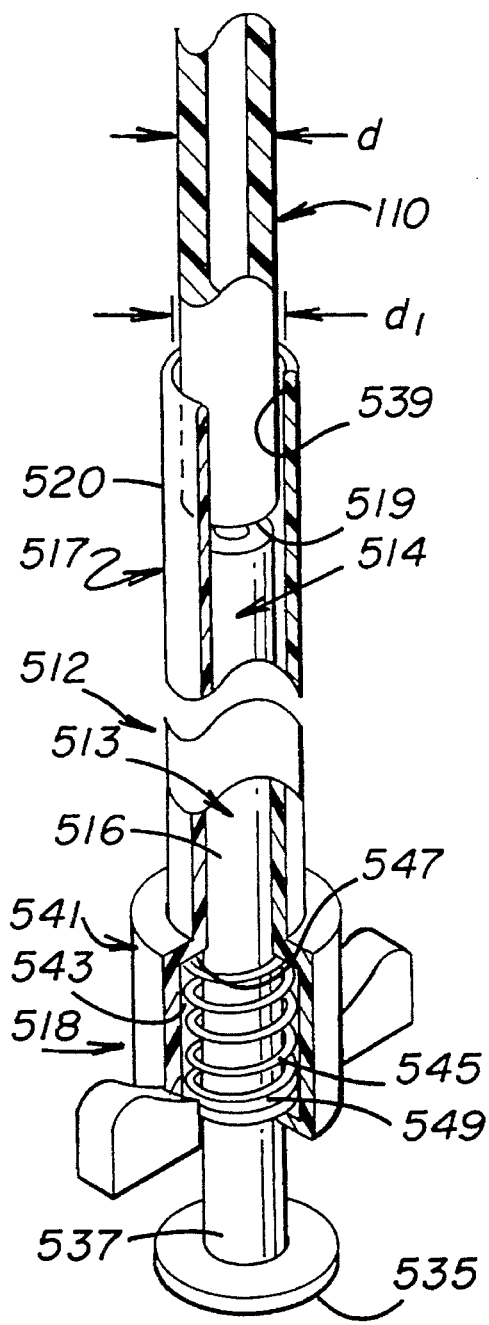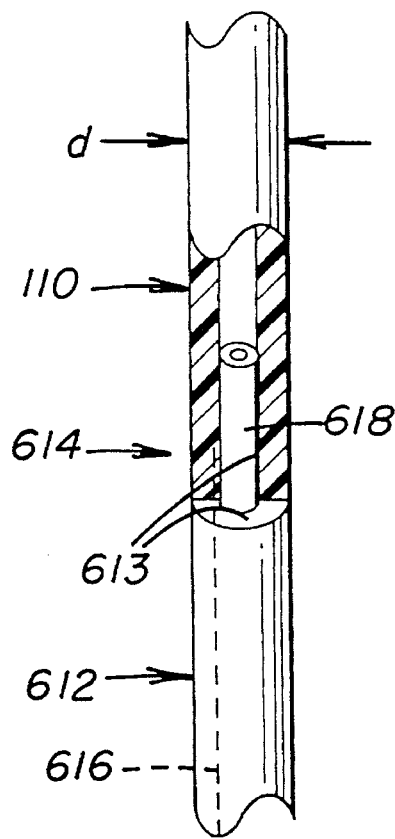
FIG. 8
FIG. 9

SOFTENING EXPANDING URETERAL STENT

TECHNICAL FIELD

This invention relates to a ureteral stent. More specifically, it relates to a stent comprising a physiologically acceptable polymer which upon hydration is capable of expanding and softening to a predetermined degree, resisting migration from the ureter, and facilitating urinary drainage from the kidney to the bladder.

BACKGROUND OF THE INVENTION

Ureteral blockage is a serious and very painful affliction and can result in death if not promptly and effectively treated. The blockage can occur for a number of reasons including the passage of kidney stones or debris from such stones into the ureter where they become entrapped, tumors growing against the outer wall of the ureter and forcing constriction and internal or ureter wall tumors. Eventually the problem is solved by surgery, medication or waiting until debris is naturally cleared from the ureter. However, a stent must often be inserted in the ureter on a temporary basis to provide drainage until the condition can be corrected.

There are many different ureteral stents available. The main function of each of these ureteral stents is to bypass ureteral obstruction and to provide urinary drainage from the kidney to the bladder for a period of time which varies but is usually of the order of a few days to several months.

There are several methods of stent placement within the ureter. One method involves passing a guide wire up the ureter into the kidney. Thereafter, a tubular stent is fed and coaxially slid up the guide wire into the ureter using a tubular stent pusher. An alternate method employs placing a tubular stent having a closed or partially tapered shut proximal end over a guide wire. The stent is thereafter advanced up into the ureter by pushing the guide wire against the closed or partially tapered shut end. Another alternate method is to place the tubular stent over the guide wire with the stent pusher over and affixed to the guide wire behind the stent and thereafter to advance the entire assemblage into the ureter. These methods can also be used, with appropriate surgery to provide access, to insert a stent from the kidney downwardly through the ureter to the bladder.

Early ureteral stents were straight. As a result, after placement into the ureter, these straight stents often migrated or were expelled from the ureter as a result of peristaltic action by the ureter. Later ureteral stents, therefore, have been designed with means of retention on one or both ends of the stent. The retention means is intended to inhibit stent migration either upward into the kidney or downward into the bladder. Retention means that have been employed are in the form of hooks, pigtails, coils, corkscrews, malecots or any other practical shape that will serve the purpose.

Ureteral stents also come in many different lengths. The variations in stent length are often necessary to accommodate the different ureter sizes in different size patients. As a result, a stock of different length ureteral stents must often be kept available. To overcome this problem of stocking many different length ureteral stents, some stents have been designed in the form of an expanding coil or corkscrew as disclosed in U.S. Pat. Nos. 4,531,933; 4,643,716; 4,671,795; and 4,813,925, or utilize connectors as disclosed in U.S. Pat. No. 4,790,810.

In addition to varying lengths, ureteral stents are also made with varying diameters, e.g., from 4.5 French (0.059") to 8.5 French (0.112"), and varying degrees of hardness. Ureteral stents with smaller diameters are usually easier to insert but may not provide sufficient drainage, whereas stents with larger diameters allow for increasing drainage capacity through the ureter but may be difficult to insert. Stiff ureteral stents are also easier to insert than are softer stents, but once inserted can lead to increased patient discomfort. Softer stents, on the other hand, provide more comfort for the patient but are more difficult to insert due to their softness. Presently, most available stents are either made of silicone as disclosed in U.S. Pat. No. 4,212,304 or of a harder polymer. Silicone may increase patient comfort, but because of the softness of silicone, it is more difficult to guide the stent into the ureter. Once in the ureter, the softness of the silicone increases the likelihood of migration of the stent because rigid retention means are not available.

To balance ease of insertion, better retention and patient comfort, some ureteral stents have been designed combining a stiff material at the kidney end for easier insertion and better retention with a softer material at the bladder end for patient comfort. These dual hardness stents are disclosed in U.S. Pat. Nos. 4,820,262; 4,874,360; and 4,931,037.

It is at times desirable or necessary to provide a stent which is wider at one end, either its proximal end or its distal end, perhaps as much as 16 French in diameter, and narrower at the other end, perhaps 4.5 French to 7 French. In the past, this has usually required insertion from the proximal (kidney) end of the ureter, a relatively difficult procedure.

Swellable ureteral stents utilizing hydrophilic polymers of the nature set forth in U.S. Pat. No. 4,377,010 and elsewhere, generally as coatings on other materials but also alone, have been investigated using piglets (See *An Experimental Study of Hydrophilic Plastics for Urological Use*, J. W. A. Ramsey, et al, British Journal of Urology, Volume 58, pp 70–74, 1986 and/or *Evaluation of Polymeric Materials for Endourologic Devices*, H. K. Mardis, Seminars in Interventional Radiology, Volume 4, Number 1, pp 36–45, March 1987) but have not received acceptance in the medical community. They have exhibited high biocompatibility. Such stents have not been formulated with different softnesses and/or swellability at different portions thereof whereby optimal comfort combined with retainability, ease of insertion and the ability to provide stents which will assume specially desired shapes on hydrating have not been available or contemplated.

Although ureteral stents have been designed to address one or more of the above problems specifically, there are currently no ureteral stents incorporating features that can bypass all of the aforementioned disadvantages. It is thus desirable to have a ureteral stent that inserts easily, can provide selectable and different degrees of softening and/or swelling on different portions of the stent, can have a tapered tip that expands, has an adequately large size once expanded, provides strong retention, can be inserted into the ureter yet can, if desired, have a significantly larger diameter at the distal and/or the proximal end upon hydration and at the same time increases patient comfort.

DISCLOSURE OF INVENTION

The present invention is directed to overcoming one or more of the problems as set forth above.

A ureteral stent is set forth in accordance with one embodiment of the invention. It comprises an elongated member having a proximal end portion and a distal end portion joined by a body portion. The elongated member has an initial member outer diameter, It includes retention means for retaining the stent within a ureter. The member is formulated of a physiologically acceptable polymer capable of hydrating with concurrent softening and with concurrent expanding from the initial member outer diameter to form a final member outer diameter. The polymer is formulated such that upon hydration the member softens or expands to a different degree at different locations therealong.

In accordance with yet another embodiment of the invention a ureteral stent is set forth. It comprises an elongated member having a proximal end portion and a distal end portion joined by a body portion. The elongated member has an initial member outer diameter, It includes retention means for retaining the stent within a ureter. The member is formulated of a physiologically acceptable polymer comprising a hydrophilic component and a non-hydrophilic component. It is capable of hydrating with concurrent softening and with concurrent expanding from the initial member outer diameter to form a final member outer diameter. The polymer is formulated such that a selectable time after hydration the final cross ureteral member outer diameter decreases to a smaller cross ureteral member outer diameter.

A ureteral stent comprises still another embodiment of the invention. It comprises an elongated member having a proximal end portion and a distal end portion joined by a body portion. The elongated member has an initial member outer diameter. The member is formulated of a physiologically acceptable polymer capable of hydrating with concurrent softening and with concurrent expanding from the initial member outer diameter to form a final member outer diameter. The polymer is formulated such that retention means for retaining the stent within a ureter form upon hydration of the stent within the ureter.

Another embodiment of the invention is in the nature of a combination of a ureteral stent and insertion means. The ureteral stent comprises an elongated member. It has a proximal end portion and a distal end portion joined by a body portion. The elongated member has a member outer diameter. The stent has retention means for retaining the stent within a ureter. The insertion means comprises an elongated pusher mechanism including a push rod having a far end portion for extending into the ureter and a near end portion. The insertion means further comprises a tubular member defining a bore and having far and near end portions. The push rod is positioned within the bore in slidable relation thereto. The far end portion of the bore has an inner diameter which is substantially equal to the outer diameter of the member so as to allow the distal end portion of the member to fit inside the bore.

Still another embodiment of the invention is a combination of a ureteral stent and insertion means. The ureteral stent comprises an elongated member having a proximal end portion and a distal end portion joined by a body portion. The elongated member has a member outer diameter. The stent has retention means for retaining it within a ureter. The insertion means comprises an elongated pusher bonded to the distal end portion of the member to form an assemblage.

An additional embodiment of the invention is a combination of a ureteral stent and insertion means. The ureteral stent comprises an elongated tubular member defining a lumen and having a proximal end portion and a distal end portion joined by a body portion. The elongated member has a member outer diameter. The stent has retention means for retaining it within a ureter. The insertion means comprises an elongated pusher having an outer diameter generally equal to the initial outer diameter of the member. The pusher has an engaging end portion joined by a handle portion. The engaging end portion has a shoulder from which a cylindrical post axially extends. The post is smaller in diameter than the diameter of the pusher. It is adapted to engage with the lumen of the member so as to allow positive engagement between the post and the lumen of the member and to allow forward and backward manipulation of the member during insertion.

The invention provides a ureteral stent that is easily insertable and upon implantation hydrates, softens and expands so as to create a clear passage within the ureter so as to increase urinary drainage from the kidney into the bladder while at the same time providing strong retention and maintaining patient comfort. If desired the stent can be formed so as to seal any openings within the ureteral wall and/or to dilate any constrictions within the ureter.

BRIEF DESCRIPTION OF THE DRAWINGS

The invention will be better understood by reference to the figures of the drawings wherein like numbers denote like parts throughout and wherein:

FIGS. 3A–3C illustrate, in views similar to FIGS. 1A–1C, a stent in accordance with yet another embodiment of the invention;

FIG. 4 illustrates, in partial view, in section, an anchoring structure useful with various embodiments of the invention;

FIG. 5 illustrates, in partial side view, another anchoring structure useful with various embodiments of the invention;

FIG. 8 illustrates, in partial view, another insertion structure useful with various embodiments of the invention;

FIG. 9 illustrates, in partial view, yet another insertion structure useful with some embodiments of the invention; and FIG. 10 illustrates, in partial view, a stent with internal ribs.

BEST MODE FOR CARRYING OUT INVENTION

Figures 1A, 1B, 1C:
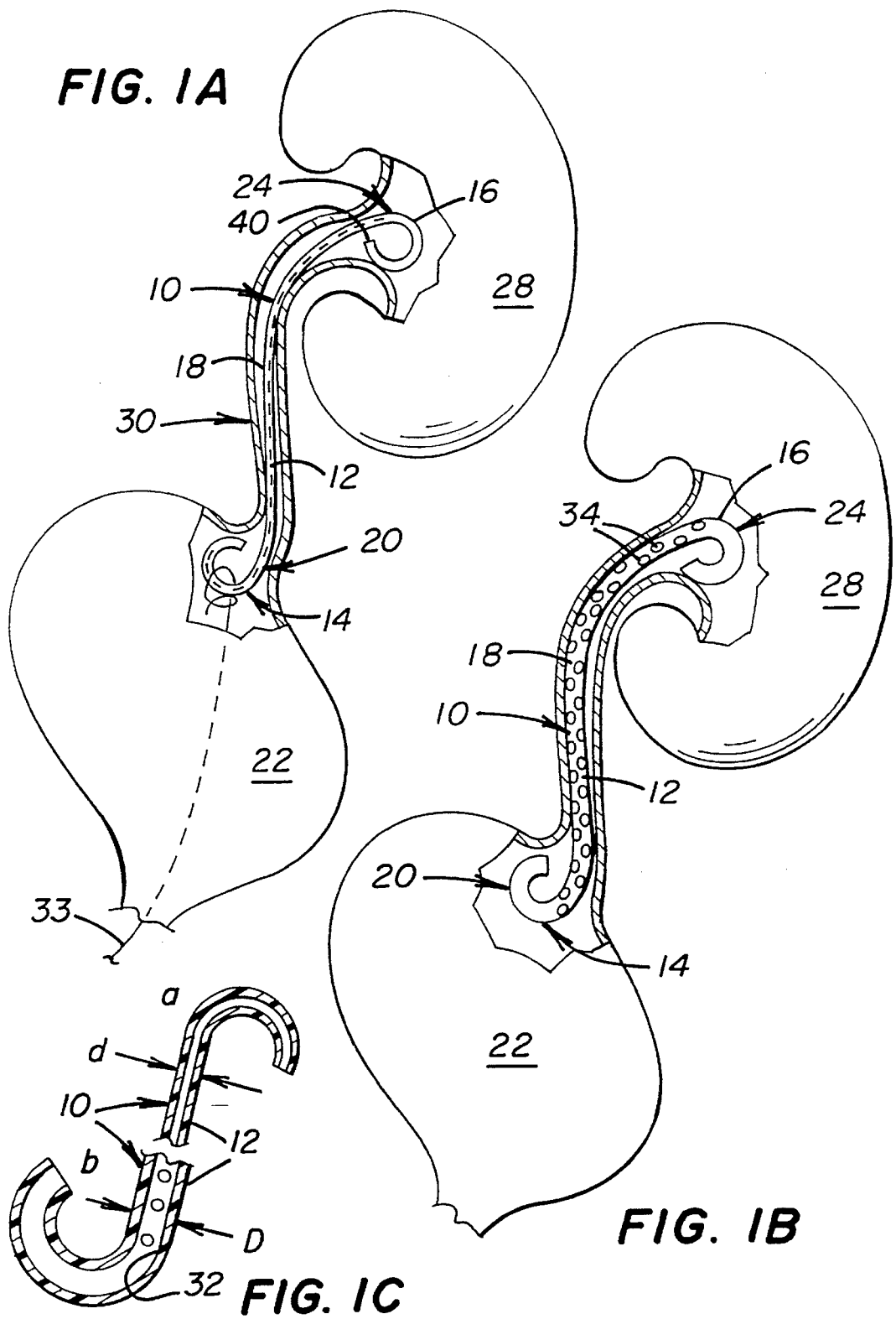
FIGS. 1A–1C illustrate, in sectional view, a stent in accordance with an embodiment of the invention after insertion in the ureter but before expansion (1A), after expansion (1B) and the stent both before (a) and after (b) expansion (1C)

The invention relates generally to a ureteral stent 10, one embodiment of which is shown in FIGS. 1A–1C. The stent 10 comprises a tubular elongated member 12 having a selected initial cross ureteral stent outer diameter d. The elongated member 12 has a proximal end portion 16 and a distal end portion 14 joined together by a body portion 18. The proximal end portion 16 includes proximal retention means 24 for retaining the proximal end portion 16 in the kidney 28. The distal end portion 14 includes distal retention means 20 for retaining the distal end portion 14 in the bladder 22. The member 12 is formulated of a physiologically acceptable polymer that is capable of expanding to a predetermined degree. Upon insertion of the stent 10 into the ureter 30, as will be seen, referring to FIG 1B and section b of FIG. 1C, the elongated member 12 hydrates and expands to form a predetermined final cross-ureteral stent outer diameter D which is selected to provide enhanced fluid passage from the kidney 28 to the bladder 22. The length of the stent 10 also generally increases upon hydration whereby the medical practitioner would start with a stent 10 somewhat shorter than that desired in the hydrated state.

A lumen 32 extends through the entire length of the stent 10 with an opening at the distal retention means 20 and a corresponding opening at the proximal retention means 24. Additionally, drainage holes 34 can cover a portion or all of the length of the stent 10. In this embodiment the fluid passage can occur through the lumen 32, the drainage holes 34 and between the wall of the ureter 30 and the exterior of the elongated member 12.

The proximal retention means 24 of this embodiment (shown here in a loop shape) comprises the proximal end portion 16 and lies in the same axial plane as does the tubular member 12. The loop shaped distal retention means 20 comprises the distal end portion 14 of the tubular member 12 and lies in the same axial plane as does the tubular member 12. The distal retention means 20 and the proximal retention means 24 may lie within the same axial plane, or may be offset if desired. The loop shaped distal retention means 20 and proximal retention means 24 may also curl in opposite directions if desired. Although the distal retention means 20 and the proximal retention means 24 are shown in a loop shape, they can, for example, be in any desired shape which will provide adequate anchoring; each may independently be selected, for example, from hook, J-curl, helical curl, pigtail, malecot or other shapes. One very suitable shape for the distal retention means 20 and for the proximal retention means 24 is a coil with a 450° (one and one quarter) turn as shown in FIG. 5. Instead of 450° the coil can have any desired amount of turning, e.g., a 540° (one and one half) turn.

The stent 10 has an initial cross-ureteral stent outer diameter d, as shown in section a of FIG. 1C, which can suitably fall within a range between about 4.5 French and about 7.0 French for ease of insertion. The distal retention means 20 and the proximal retention means 24, both of which are flexible, have an initial curl diameter which is substantially larger than the initial cross-ureteral stent outer diameter d of the tubular member 12.

The stent 10 is formulated from a physiologically acceptable polymer that is capable of softening to a predetermined degree and expanding, from generally in within forty five (45) minutes to a few hours after insertion into the ureter 30, to form a predetermined final cross-ureteral stent outer diameter D selected to provide patient comfort and to enhance fluid passage from the kidney 28 to the bladder 22. The polymer comprises a hydrophilic component capable of hydrating and expanding the selected initial cross-ureteral diameter, for example, from about five percent (5%) to about three hundred percent (300%). The stent 10 can, for ease of insertion, initially be even stiffer than the stiff stents of the past (usually 100 Shore A to 70 Shore D) since it does not remain hard to cause discomfort to the patient once hydration has occurred.

The hydrophilic component is suitably a polymer that absorbs at least about thirty percent (30%) water, preferably at least about fifty percent (50%) water, more preferably about one hundred percent (100%) water or more, e.g., one hundred fifty percent (150%) water, by weight based on the weight of the hydrophilic polymer. The hydrophilic polymer is capable of forming a hydrogel on absorption of water.

The hydrophilic polymer can suitably be selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, a starch such as cornstarch, a modified starch, an alginate, a hydroxy ethyl carbohydrate, or the like. Copolymers of the monomers forming such polymers are also suitable. Mixtures of any of the above are likewise suitable. The polymer should preferably allow the stent 10 to swell to a selected percent after hydration.

The degree of swelling of the stent 10 can also be controlled or tailored as desired by controlling the amount of cross-linking of the polymer. The amount of cross-linking can be adjusted, as is well known in the art, chemically and/or by adjusting the amount of radiation applied to cause the cross-linking. The higher the degree of cross-linking, the less will be the swellability of the hydrated polymer and thus of the stent 10.

The stent 10 preferably comprises a hydrophilic component and a non-hydrophilic component in a selected ratio. The ratio of hydrophilic component to non-hydrophilic component is preferably adjustable so as to allow the polymer to expand the initial cross ureteral stent outer diameter d to a desired extent, for example, by from about five percent (5%) up to about three hundred percent (300%) upon hydration.

The polymer can be formulated so that upon hydration one portion of the stent 10, for example, the distal retention means 20, softens to a greater degree than does another portion of the stent 10, for example, the proximal retention means 24. To achieve this dual hardness after hydration, initially the ureteral stent 10 can be processed differently at the proximal end portion 16 than at the distal end portion 14. For example, the proximal retention means 24 can be cross-linked more than is the distal retention means 20, e.g., by exposing it to more polymerization initiating radiation.

The stent 10 can be formulated of a polymer which comprises only a hydrophilic component. However, it will preferably also comprise a non-hydrophilic component. The non-hydrophilic component comprises a polymer which does not substantially absorb or attract water. Preferably, the non-hydrophilic polymeric component is capable of absorbing water in an amount of no more than about thirty percent (30%), more preferably no more than about fifteen percent (15%) and still more preferably no more than about ten percent (10%), by weight, based on the weight of the non-hydrophilic polymeric component.

The non-hydrophilic component can be, for example, a thermosetting elastomer such as silicone, a polyurethane such as an aliphatic or aromatic polyurethane, a polyether polyurethane, a polyester polyurethane; an ethylene copolymer such as ethylene-vinyl acetate copolymer; a polyamide, in particular a polyamide of low crystallinity; an aliphatic polyester or mixtures or copolymers thereof.

The proximal retention means 24 of ureteral stent 10 can be exposed to a larger dose of electron beam cross-linking radiation whereas the distal retention means 20 can be exposed to a smaller dose, for example, by shielding it. The larger dose of electron beam cross-linking radiation yields a relatively stiffer proximal retention means 24 which softens to a lesser degree than does the distal retention means 20 upon hydration. Consequently, retention strength by the proximal retention means 24 within the kidney 28 is increased. The smaller dose of electron beam cross-linking radiation yields a relatively softer distal retention means 20 and allows it to soften to a greater degree than does the proximal retention means 24 upon hydration thereby providing increased patient comfort.

Examples of swelling (and softening) polymers having both hydrophilic and non-hydrophilic components and which are useful in the practice of the invention are those described in, for example, U.S. Pat. No. 4,883,699, issued Nov. 28, 1989 which is incorporated herein by reference.

This patent discloses a suitable composition for the polymer which comprises:

(a) a first phase which comprises a substantially non-hydrophilic polymeric component; and (b) a second phase which comprises a hydrophilic polymeric component;

said material (i) being capable of absorbing water to an extent that it swells with a swelling ratio of at least about 1.3:1, preferably from about 1.5:1 to 3.5:1 (and generally softens with a softening ratio of at least about 2:1)

Also useful are those swelling and softening hydrophilic polymers described in U.S. Pat. Nos. 4,359,558; 4,424,305; 4,454,309 and 4,439,583 of Tyndale Plains-Hunter Ltd. incorporated herein by reference. The preferred polymer composition of these patents essentially comprises a polyurethane diacrylate composition having from about ninety (90) to about sixty five (65) weight percent of a hydrophilic polyurethane resin and from about ten (10) to about thirty five (35) weight percent of a diacrylate.

Still another polymer which is suitable is the thermoplastic elastomeric hydrophilic polyurethane described in U.S. Pat. No. 5,061,254 of Becton-Dickenson and Company which is incorporated herein by reference.

In accordance with one embodiment of the invention, the stent 10 can be formulated of a physiologically acceptable polymer that is capable of softening and expanding to a predetermined degree upon hydration then subsequently shrinking to a desired extent, for example, to roughly its non-hydrated size, to allow it to be readily withdrawn from the patient after a desired length of time. To accomplish this, the polymer can comprise a soluble hydrophilic component and a non-soluble non-hydrophilic component having softening and expansion characteristics as previously described. The hydrophilic component and non-hydrophilic component can be selected from the respective groups indicated above. As the hydrophilic component dissolves or degrades the stent 10 will then shrink.

As another alternative, the stent 10 can be formulated of a central cylindrical core of a physiologically acceptable polymer that is capable of softening and expanding to a predetermined degree upon hydration but that will not dissolve or biodegrade readily in the ureter. The stent 10 can further include an outer layer formulated of a physiologically acceptable polymer that is readily soluble or biodegradable in the ureter. For example, the outer layer can be a substantially non-cross-linked hydrophilic polymer. The dissolving of all or part of the outer layer then leads to a subsequent-to-insertion shrinking of the stent 10 to a desired extent, for example, to roughly its non-hydrated size, to allow it to be readily withdrawn from the patient after a desired length of time.

The expansion and softening of a non-hydrated stent 10 normally occur from within forty five (45) minutes to a few hours after its insertion into the ureter 30. The subsequent shrinking of stent 10 to its non-hydrated size or smaller usually takes from three days to three months as the soluble (or degradable—the term soluble is used herein to encompass all means by which the stent 10 shrinks) component is dissolved or degraded from the stent 10. The rate of shrinking and the final shrink size can be controlled by the volume ratio of hydrophilic component to non-hydrophilic component and/or the extent to which the hydrophilic component is cross-linked. The higher the initial volume of soluble component, the smaller the size of the stent 10 after the soluble component has dissolved. In addition, the higher the degree to which the soluble component is cross-linked, the slower the rate at which the soluble component will dissolve and thus the slower the rate at which the stent 10 will shrink.

The body portion 18 of ureteral stent 10 that comprises a hydrophilic component can be formulated such that the proximal end portion 16 expands preferably by up to about three hundred percent (300%) to form a final proximal end outer diameter. Alternatively, the body portion 18 can be formulated such that the distal end portion 14 expands preferably by up to about three hundred percent (300%) to form a final distal end outer diameter. If desired, both the proximal end portion 16 and the distal end portion 14 can be made to expand by up to three hundred percent (300%), but not necessarily to the same degree. The final proximal or distal end outer diameter is necessary in certain situations so as to allow the sealing of any openings within the ureteral wall and/or the dilating of any constrictions at the respective end of the ureter. This expansion can be accomplished by controlling the degree of cross-linking, e.g., by controlling the relative amounts of radiation as with the proximal retention means 24 and the distal retention means 20.

The body portion 18 of stent 10 that comprises a hydrophilic component and a non-hydrophilic component can similarly be cross-linked to have its proximal end portion 16 or distal end portion 14 or both expand by up to three hundred percent (300%). However, the expansion of the proximal end portion 16 and/or distal end portion 14 can also be controlled by beginning with a non-hydrated stent 10 with substantially a constant outer diameter along its length, heating the non-hydrated stent 10 above the forming temperature of the non-hydrophilic component, which is above the melting temperature of the hydrophilic component, while in contact with a first mandril which molds it into having an enlarged diameter towards its proximal end portion 24, cooling the stent 10 to below the melting temperature of the hydrophilic component while it is still shaped by the first mandril, removing the stent from the first mandril, positioning the stent 10 on a second mandril which defines substantially an equal diameter along its entire length, heating the stent 10 to a temperature above the melting temperature of the hydrophilic component but below the forming temperature of the non-hydrophilic component, molding the stent 10 against the second mandril such that it has substantially an equal diameter along its entire length and cooling the stent 10 to a temperature below the melting temperature of the hydrophilic component while it is still shaped by the second mandril. On later insertion into the body, hydration of the hydrophilic component, which substantially reduces the strength of the shape set by the hydrophilic component, allows the shape molded against the second mandril to be lost and the stent 10 returns to the shape molded against the first mandril. A similar technique can be used to form the funnel shape retention means 214, 216 of FIGS. 3A–3C.

The stent 10 can be formed so as to have no increase in length following insertion. This can be accomplished by having the physician partially uncoil the proximal retention means 24 and/or the distal retention means 20. If, for example, the coil initially has a 450° (one and one quarter) turn as shown in FIG. 5, the proximal retention means 24 and/or the distal retention means 20 can be partially straightened, for example, 90° (one quarter turn) to provide a somewhat lengthened stent and then on hydrating after insertion the coil will curl back to the 450° turn to compensate for the length increase of the stent 10.

As with prior art stents, a suture 33, shown in FIG. 1, can be attached to the distal end portion 14 of the stent 10 so as to allow it to be removed without the use of a cystoscope.

Figure 2A:
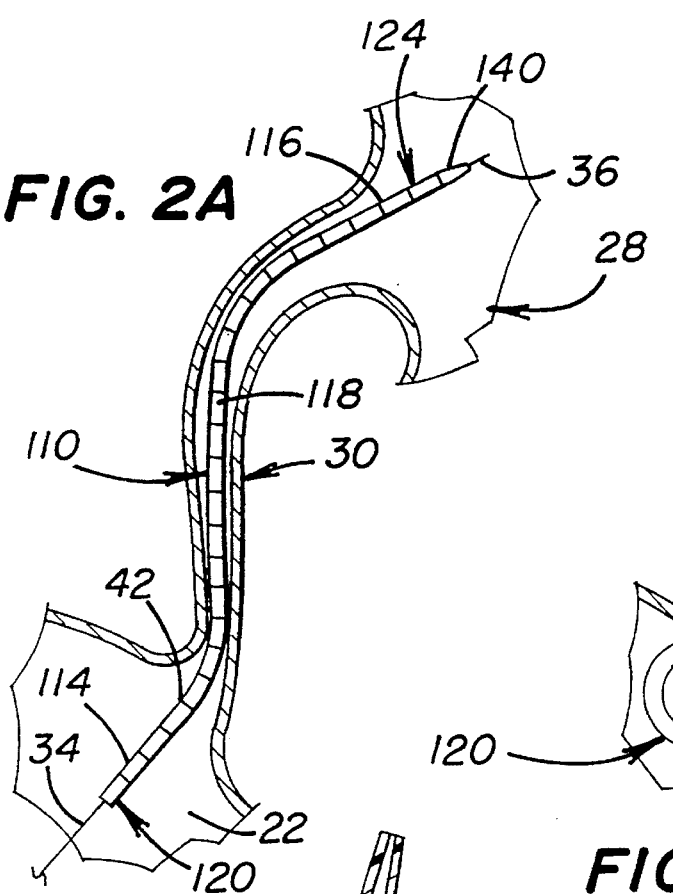
FIGS. 2A–2D illustrate, in sectional view, a stent in accordance with another embodiment of the invention after insertion in the ureter but before expansion (2A), after expansion (2B), the stent both before (a) and after (b) expansion (2C) and the insertion of the stent (2D)
Figure 2B:
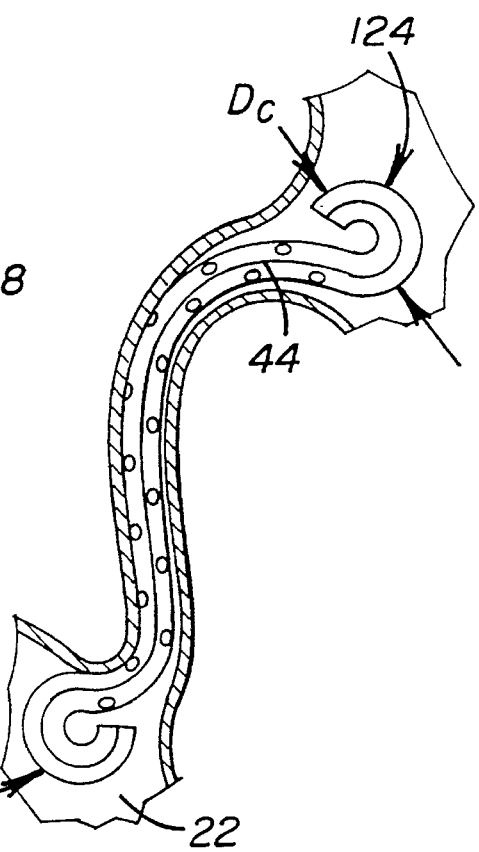
Figure 2C:
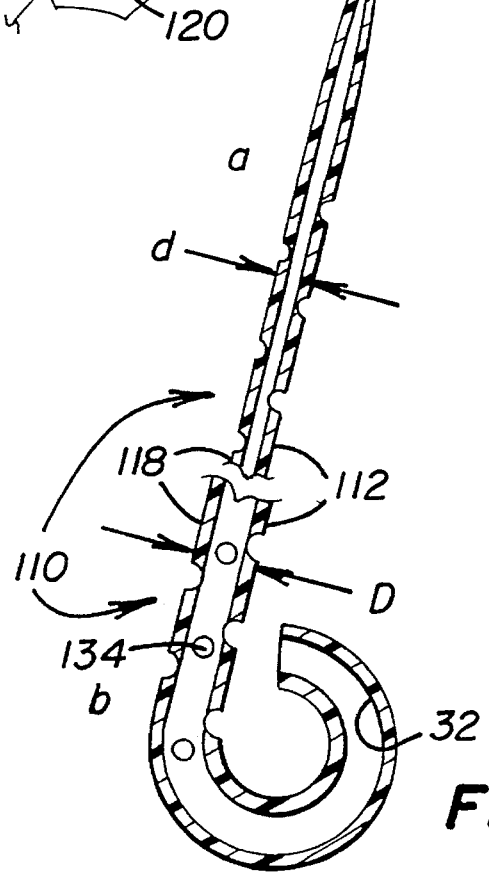
Figure 2D:
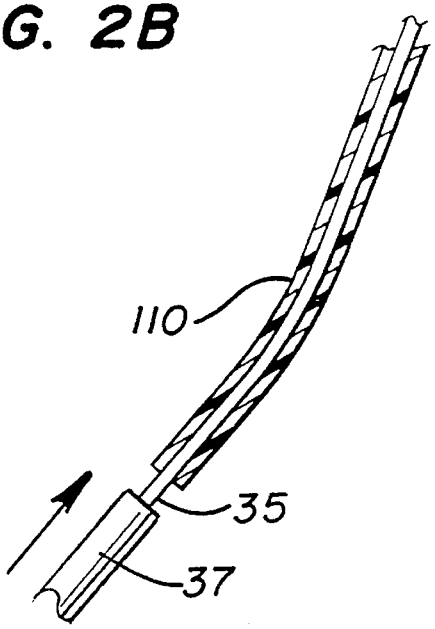

Referring to FIGS. 2A and 2D (which illustrate an embodiment somewhat different than that of FIGS. 1A–1C as will be explained later), one preferred method to place stent 110 in the patient is to insert a guide wire 35 into the patient up the ureter 30 with a proximal tip 36 of the guide wire 35 going into the kidney 28 and stopping. The stent 110 is then drawn over the distal end of the guide wire 35 to straighten the loop shaped proximal retention means 124 and the loop shaped distal retention means 120. Once the stent 110 is straightened over the guided wire 35 the stent 110 is pushed, using a tubular stent pusher 37, and thereby advanced over the guide wire 35 into the patient and into the ureter 30 stopping with its proximal end portion 116 in the kidney 28. The proximal end 140 of the proximal retention means 124 in FIG. 2A can be tapered, so as to facilitate ease of insertion into the ureter 30. This can assist in the reduction of trauma to the tissues of the ureter 30. The tapered proximal end 140 may be formed through the application of shape memory technology described earlier such that upon hydration the tapered proximal end 140 expands to a diameter substantially similar to the final cross-ureteral stent outer diameter D of stent 110.

Stent 110 may also incorporate internal ribs 142 within the lumen 32 longitudinally along the body portion 118 as illustrated in FIG. 10 so as to reduce the chance of kinking while the stent 110 is advanced into the ureter 30. Kinking is not desirable since drainage from the kidney 28 to the bladder 22 can be inhibited.

As the stent 110 is advanced into the ureter 30 the progress of the stent 110 can be measured by using length markers 42 (FIG. 2A) longitudinally imprinted on the stent 110. With the stent 110 properly positioned in the ureter 30 as shown in FIG. 2A, the guide wire 35 can be removed. As the guide wire 35 is removed, the proximal retention means 124 reforms the loop shape and hydrates as illustrated in FIG. 2B. The formation of the loop shape by the proximal retention means 124 in the appropriate position can be verified by fluoroscopic examination. As the guide wire 35 is further removed, the formation of the loop shape by the distal retention means 120 also takes place. The position of the distal retention means 120 can also be verified by observing a medial stripe 44 (FIG. 2B) down the length of the stent 110.

Figure 6A:
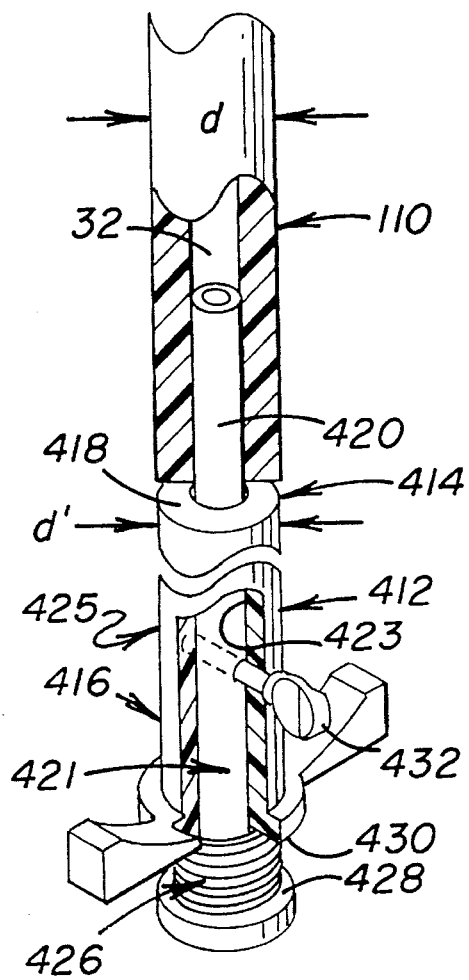
FIGS. 6A and 6B illustrate, in partial view in two different positions of operation, an insertion structure useful with various embodiments of the invention.
Figure 6B:
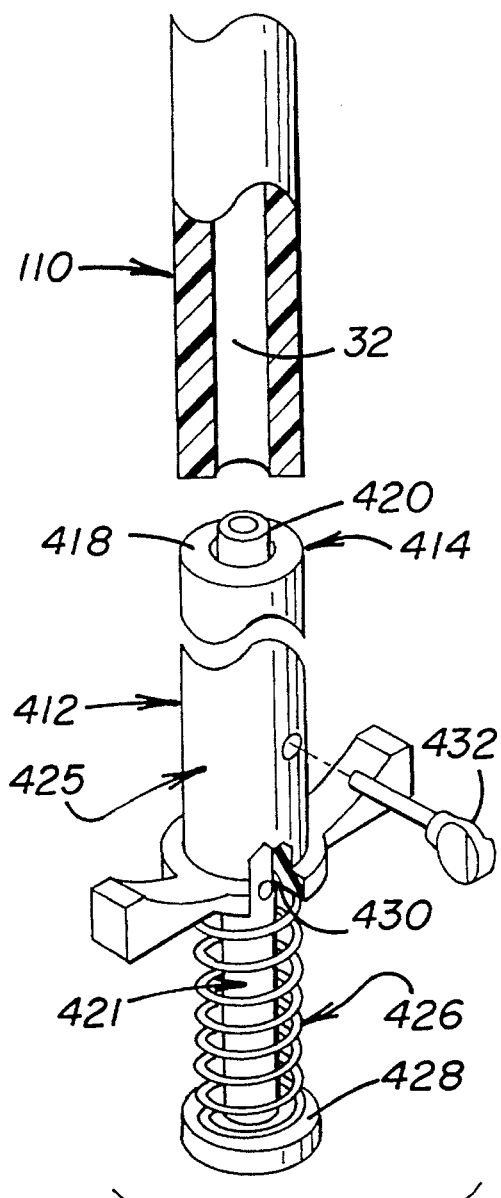

Referring to FIGS. 6A and 6B, stent 110 may also be suitably placed within the ureter 30 utilizing a two piece stent pusher module 412 as illustrated. The pusher module 412 comprises a distal (to the user) end portion 414 joined by a generally straight handle portion 416. The handle portion 416 has an outer diameter d' similar to the initial cross ureteral stent outer diameter d of stent 110. The distal end portion 414 includes a shoulder 418 from which a generally cylindrical post 420 extends. The post 420 is the far end portion of a piston like member 421 which is in sliding fit within a bore 423 in a tubular member 425 which also forms a part of the pusher module 412. The cylindrical post 420 fits firmly within the lumen 32 of the stent 110 so as to allow positive engagement between the pusher module 412 and the stent 110. The positive engagement between the pusher module 412 and the stent 110 allows for forward and backward manipulation of the stent 110 during insertion. Once the stent 110 is correctly positioned within the ureter 30, the two piece pusher module 412 can be disengaged from the stent 110 by either pulling against the handle portion 416 or by retracting the post 420 to the position shown in FIG. 6B. In the embodiment illustrated the piston like member 421 fits within the tubular member 425. A spring 426 is compressed between a flange 428 on a proximal end portion 422 of the piston like member 421 and a facing flange 430 on the tubular member 425. A pin 432 fits through a lateral hole in the tubular member 425 and engages in a cavity in the piston like member 421. When disengagement of the pusher module 412 from the lumen 32 is desired, the user merely removes the pin 432 while holding the tubular member 425 from moving. The spring 426 then impels the post 420 out of engagement with the stent 110. Alternatively, the spring/pin mechanism can be omitted and the post 420 can be removed, while holding the pusher module 412 in place, by pulling upon it. Alternatively, the pusher module 412 can be removed once the stent 110 hydrates and expands. The expansion of the stent 110 loosens the pusher module 412 therefrom and the pusher module 412 can be easily removed thereafter. As illustrated, a longitudinal bore can be formed through the entire assembly, if desired, to allow for over the wire insertion.

Figure 7:
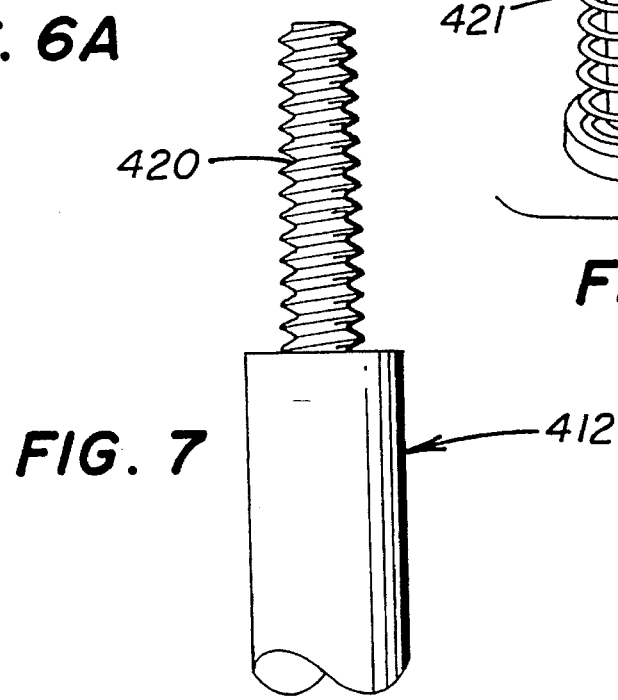
FIG. 7 illustrates, in partial view, a variation of the insertion structure of FIG. 6.

Although shown as having a smooth outer surface, the cylindrical post 420 can be threaded as shown in FIG. 7 so as to allow a tighter engagement between the pusher module 412 and the stent 110. Removal of the pusher module 412 then requires disengagement by unscrewing the pusher module 412 from the stent 110 or awaiting hydration. The spring arrangement of FIGS. 6A, 6B would not be present.

FIG. 8 illustrates another suitable pusher module 512 for maneuvering the stent 110 into the ureter 30. One embodiment of the pusher module 512 comprises a push rod 513 having a distal (to the user) end portion 514 joined by a handle portion 516. The pusher module 512 also includes a sleeve 517 having a bore 519 in which the push rod 513 slidingly fits. A disengaging mechanism 518 is located about the handle portion 516 of the push rod 513. The push rod 513 extends between the distal end portion 514 and a push end 535 at a proximal end portion 537 of the handle portion 516. The bore 519 has an inner diameter $d_1$, at least at a distal end portion 539 thereof, which is substantially equal to the initial outer diameter d of the stent 110 so as to allow a firm fit between the stent 110 and the distal end portion 539 of the bore 519. The disengaging mechanism 518 is encased within a proximal end portion 541 of the sleeve 517. It is in the nature of a chamber 543 in which a spring 545 is located about the push rod 513. The spring 545 normally biases the push rod 513 proximally (to the user) in the bore 519 by acting between a shoulder 547 defined by the chamber 543 and a flange 549 which extends from the push rod 513 and is located within the chamber 543. To disengage the stent 110 the user pushes the push end 535 of the push rod 513 relatively toward and further into the sleeve 517 while maintaining the sleeve 517 essentially stationary. This compresses the spring 545 and the distal end portion 514 of the push rod 513 impels the stent 110 out of the bore 519. As illustrated, a longitudinal bore can be formed through the entire assembly, if desired, to allow for over the wire insertion.

Referring to FIG. 9 there is shown still another suitable pusher 612 for maneuvering the stent 110 into the ureter 30.

One end of the pusher 612 is bonded at 613 to one end of the stent 110 forming an assemblage 614. The assemblage generally has the same outer diameter as the initial diameter d of the stent 110. The assemblage 614 can optionally include a suture 616, illustrated by a dashed line, extending from the stent 110 and imbedded longitudinally down the pusher 612. The pusher 612, if desired, may include a cylindrical portion 618, similar to that shown in FIGS. 6A and 6B, to enhance the firmness of the bonding between the stent 110 and the pusher 612. The pusher 612 is formulated of a body fluid soluble or biodegradable polymer capable of dissolving or degrading within a limited time after insertion of the assemblage 614 into the ureter 30. Once the pusher 612 is degraded, the stent 110 and the suture 616 remain within the ureter 30. The suture 616 being attached to the ureteral stent 110 extends to the outside of the patient so as to allow its removal without using a cystoscope. As illustrated, a longitudinal bore can be formed through the entire assembly, if desired, to allow for over the wire insertion.

Usable biodegradable polymers include polyorthoesters, polylactides, polyglycolides and copolymers, collagen, polycaprolactone and polyglutonates. One suitable biodegradable polymer comprises L(-)lactide, glycolide and epsilon-caprolactone in selected ratios. An example of a biodegradable polymer having L(-)lactide, glycolide and epsilon-caprolactone which is useful in the practice of the invention is described in U.S. Pat. No. 5,085,629 issued Feb. 4, 1992 which is incorporated herein by reference.

Suitable dissolvable polymers include polyethylene oxides, polyvinylacetates, polyvinylpyrrolidone, polyethylene oxide based polyether urethanes, starches and cellulose derivatives such as hydroxyethyl cellulose. The dissolvable polymers are generally preferred since they can be readily formulated so as to dissolve in minutes to hours. The rate at which the polymer hydrates and degrades can be controlled by controlling the molecular weight and the amorphous nature of the pusher 612 composition to assure the integrity of the pusher 612 as it aids in advancing the stent 610 into the ureter 30.

After it is properly positioned within the ureter 30, the stent 110 as shown in FIG. 2A has its proximal retention means 124 extend beyond the ureter 30 into the kidney 28. Similarly the distal retention means 120 extends beyond the ureter 30 into the bladder 22.

Confirmation that the stent 110 has been correctly positioned within the ureter 30 can also be obtained by x-ray or by fluoroscopy. If desired, a radiopaque material can be incorporated into the stent 110 or can be present as the measurement markings 44 along the length of the stent 110 so as to render the stent 110 visible during x-ray or fluoroscopic examination. The radiopaque material can suitably be selected from the group consisting of barium sulfate, bismuth subcarbonate, tantalum, tungsten, silver or mixtures thereof. The radiopaque material can be incorporated into the polymer from which the stent 10 is formed by melt mixing or, in the case of gels by dispersing into the gels prior to cross-linking them.

The body portion 118, being generally cylindrical in shape, has an initial cross-ureteral stent outer diameter d (see FIG. 2C), the initial cross-ureteral stent outer diameter being the initial outer diameter of the tubular member 112. As the stent 110 hydrates, referring to FIG. 2B, the body portion 118 expands radially to a final cross-ureteral outer diameter D, suitably to 6 French or more, with the precise size being selected in view of the size of the patient's ureter 30. Such expansion clears and restores the ureteral passage from the kidney 28 to the bladder 22. The body portion 118, upon hydration, also softens appropriately, for example to a hardness in the range from about 50 to about 100 Shore A. This considerably improves comfort within the patient.

The stent 110 as shown in FIGS. 2A–D may also incorporate drainage holes 134 throughout. Upon hydration, as the stent 110 expands, the drainage holes 134 also expand. As a result, the size of the drainage holes 134 increases. The presence of larger drainage holes 134 is desirable since the rate of drainage between the kidney 28 and the bladder 20 will increase.

Referring again to FIG. 2B, the distal retention means 120 and the proximal retention means 124 may expand to selected curl diameters Dc (not necessarily equal to one another), upon hydration. However, the proximal retention means 124 does not necessarily have to expand. The selected curl diameter is substantially larger than the ureter diameter so as to prevent the stent 110 from migrating or being expelled from the ureter 30. The proximal retention means 124, possibly by being initially exposed to a greater dose of electron beam cross-linking radiation, can remain relatively stiff and soften to only a hardness which generally falls in a range from about 70 Shore A to about 70 Shore D. The distal retention means 120, being initially exposed to a lesser dose of electron beam cross-linking radiation, suitably softens to a hardness which falls in a range from about 30 to about 100 Shore A.

The stent 110 of FIGS. 2A–2D differs from the stent 10 in FIGS. 1A–1C in that the loop shaped proximal retention means 124 and distal retention means 120 of stent 110 of FIGS. 2A–2D do not exist in stent 110 in its initial form. Instead, stent 110 is initially a substantially straight cylindrical tube. Upon hydration, the proximal end portion 116 of stent 110 and the distal end portion 114 of the stent 110 expand and curl to form the proximal retention means 124 and the distal retention means 120, respectively.

The formation of the proximal retention means 124 and/or the distal retention means 120 can be achieved through the shape memory technique by utilizing the thermal properties of the hydrophilic component and the non-hydrophilic component as described earlier.

As an alternate, the formation of the proximal retention means 124 and/or distal retention means 120 can be attained by using a composition having both a hydrophilic component and a non-hydrophilic component. As discussed previously, such a composition can expand upon hydration. The higher the percentage of the hydrophilic component, other factors being equal, the more the composition expands. As a result, the degree of expansion can be controlled or tailored as desired by controlling the amount of hydrophilic component.

To form the proximal retention means 124, the proximal end portion 116 can be made such that in a cross section of the proximal end portion. 116, there is substantially more hydrophilic component on one side, preferably fifty percent (50%) to ninety percent (90%) of the composition, than on the other side. The distal end portion 114 can be similarly made if desired. The higher percentage of hydrophilic component on one side is desirable so as to allow the composition on that side to expand upon hydration by from about five hundred percent (500%) to about eight hundred percent (800%) causing the proximal end portion 116 and/or the distal end portion 114 to curl and form the proximal retention means 124 and/or the distal retention means 120 respectively.

A third embodiment of the stent of the present invention is shown in FIGS. 3A–3C. Similar to the stent 110 of FIGS. 2A–2D, the stent 210 of FIGS. 3A–3C differs from stent 110 in that the coil shaped distal retention means 220 and the coil shaped proximal retention means 224 of stent 110 do not initially exist in stent 210. Instead, the proximal end portion 216 and the distal end portion 214 of stent 210 can flare outwardly as shown to a diameter larger than the initial tube outer diameter d of the body portion 218 of the stent 210. FIGS. 3B–3C show that upon hydration the body portion 218 expands radially from an initial tube outer diameter d to a final tube outer diameter D. The distal end portion 214 and the proximal end portion 216 also expand in width (and can, but do not necessarily, contract in length) into the shape of a funnel which serves as the proximal retention means 224 within the kidney 28 and the distal retention means 220 within the bladder 22. The funnel shape retention means 220,224 of stent 210 also act to facilitate drainage. If desired, the stent 210 can be perforated throughout as shown in FIGS. 3B and 3C to further facilitate drainage.

Alternatively, a stent 310 as illustrated in FIG. 4 can have, instead of the funnel shape proximal retention means 224, an inverted tripod (or other multipod) shape proximal retention means 324. The tripod shape proximal retention means 324 has three similarly shaped pods 301 which form upon hydration. This facilitates drainage. Similarly, a tripod shape distal retention means 320 can be provided for the bladder 22.

An added attribute and advancement provided by the stents of the invention is that medicaments and/or antimineralization chemicals can be incorporated into the hydrophilic or partially hydrophilic polymers or can be deposited or otherwise provided on their surfaces. Incorporation into the polymers can be accomplished by any of a number of techniques including soaking in, surface coating, melt mixing and/or chemical grafting.

Mineralization, or more specifically calcification, particularly calcium apatite formation, can be inhibited by various chemicals. These chemicals can be incorporated into stents by the various methods referenced above. Anti-calcification chemicals or additives are known in the art and include certain diphosphonates, especially ethanehydroxy diphosphonate (EHDP), certain metal ions, especially aluminum and iron and alpha amino oleic acid derivatives to name but a few. For example, hydroxyethylidene biphosphonic acid dispersed in polyurethane (PU) articles inhibits calcification of the polymer and of the surrounding tissue and EHDP can diffuse through PU membranes and inhibit calcification of tissue. Aluminum or iron ions and oleic acid compounds have all been reported to reduce calcification of bioprosthetic porcine heart valves.

INDUSTRIAL APPLICABILITY

The ureteral stent 10 in any of its embodiments provides relief from obstructions within the ureter 30. Once properly positioned within the ureter 30, the ureteral stent 10 allows bypass of any obstructions. After expansion and/or formation of the retention means 20, 24, the ureteral stent 10 provides and maintains a clear pathway within the ureter 30, allowing sustained urinary drainage from the kidney 28 to the bladder 22.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A ureteral stent comprising an elongated member having a proximal end portion and a distal end portion joined by a body portion, the elongated member having an initial member outer diameter and including retention means for retaining the stent within a ureter, the member being formulated of a physiologically acceptable polymer capable of hydrating with concurrent softening and with concurrent expanding from the initial member outer diameter to form a final member outer diameter, the polymer being formulated such that upon hydration the member softens and expands to different degrees at different locations therealong, wherein the elongated member has an initial stiffness above about 100 Shore A and wherein upon hydration the initial stiffness of the distal end portion softens to a final softness which falls below 100 Shore A.

2. A ureteral stent comprising an elongated member having a proximal end portion and a distal end portion joined by a body portion, the elongated member having an initial member outer diameter and including retention means for retaining the stent within a ureter, the member being formulated of a physiologically acceptable polymer capable of hydrating with concurrent softening and with concurrent expanding from the initial member outer diameter to form a final member outer diameter, the polymer being formulated such that upon hydration the member softens and expands to different degrees at different locations therealong, wherein upon hydration the proximal end portion softens to about 70 Shore A to about 70 Shore D, and wherein upon hydration the distal end portion softens to about 30 to about 100 Shore A.

3. A ureteral stent comprising an elongated member having a proximal end portion and a distal end portion joined by a body portion, the elongated member having an initial member outer diameter and including retention means for retaining the stent within a ureter, the member being formulated of a physiologically acceptable polymer capable of hydrating with concurrent softening and with concurrent expanding from the initial member outer diameter to form a final member outer diameter, the polymer being formulated such that upon hydration the member softens and expands to different degrees at different locations therealong wherein the polymer comprises a hydrophilic component and a non-hydrophilic component in a selected ratio, the ratio of hydrophilic to non-hydrophilic component being selected such that upon hydration the polymer softens and expands the initial member outer diameter by from about 5% up to about 300%, and wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, starches, modified starches, alginates, hydroxy ethyl carbohydrates and mixtures and copolymers thereof and the non-hydrophilic component is selected from the group consisting of silicone, an aliphatic polyurethane, an aromatic polyurethane, a polyether polyurethane, a polyester polyurethane, an ethylene copolymer, a polyamide, an aliphatic polyester or mixtures or copolymers thereof.

4. A ureteral stent as set forth in any one of claims 1, 2, or 3, wherein the retention means is formed upon hydration of the member.

5. A ureteral stent as set forth in any one of claims 1, 2, or 3, wherein the proximal end portion is tapered to a diameter smaller than the initial outer diameter of the body portion.

6. A ureteral stent as set forth in claim 5, wherein the tapered proximal end portion upon hydration expands to an outer diameter equal to the final outer diameter of the member.

7. A ureteral stent as set forth in any one of claims 1, 2, or 3, wherein the proximal retention means is formed upon hydration into the shape of a funnel.

8. A ureteral stent as set forth in any one of claims 1, 2, or 3, wherein the proximal end portion is flared outwardly to a diameter larger than the initial outer diameter of the body portion.

9. A ureteral stent as set forth in any one of claims 1, 2, or 3, wherein the retention means includes the proximal end portion formed upon hydration into the shape of a multipod.

10. A ureteral stent as set forth in any one of claims 1, 2, or 3, wherein the polymer comprises a hydrophilic component and a non-hydrophilic component and wherein the final cross ureteral member outer diameter decreases to a smaller cross ureteral member outer diameter a selectable time after hydration within a ureter.

11. A ureteral stent as set forth in claim 10, wherein the decrease results from the dissolving of all or a portion of the hydrophilic component after hydration.

12. A ureteral stent as set forth in claim 10 wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate)., hydroxy ethyl cellulose, hydroxy propyl cellulose, methoxylated pectin gels, agar, starches, modified starches, alginates, hydroxy ethyl carbohydrates and mixtures and copolymers thereof and the non-hydrophilic component is selected from the group consisting of silicone, an aliphatic polyurethane, an aromatic polyurethane, a polyether polyurethane, a polyester polyurethane, an ethylene copolymer, a polyamide, an aliphatic polyester or mixtures or copolymers thereof.

13. A combination of a ureteral stent as set forth in any one of claims 1, 2, or 3 and insertion means, wherein the member is tubular and defines a lumen and wherein the insertion means comprises an elongated pusher having an outer diameter generally equal to the initial outer diameter of the member, the pusher having an engaging end portion joined by a handle portion, the engaging end portion having a shoulder from which a cylindrical post axially extends, the post being smaller in diameter than the diameter of the pusher and being adapted to engage with the lumen of the member so as to allow positive engagement between the post and the lumen of the member and to allow forward and backward manipulation of the member during insertion.

14. A combination of ureteral stent and insertion means as set forth in claim 13, wherein the post is threaded.

15. A combination of ureteral stent and insertion means as set forth in claim 13, including:
   biasing means for biasing the post out of engagement with the lumen; and
   removable locking means for preventing the biasing means from moving the post out of engagement with the lumen.

16. A combination of a ureteral stent as set forth in any one of claims 1, 2, or 3 and insertion means, wherein the insertion means comprises an elongated pusher mechanism which comprises:
   a push rod having a far end portion for extending into a patient and a near end portion; and
   a tubular member defining a bore and having far and near end portions, the push rod being positioned within the bore in slidable relation thereto, the far end portion of the bore having an inner diameter which is substantially equal to the outer diameter of the member so as to allow the distal end portion of the member to fit inside the bore.

17. A combination of ureteral stent and insertion means as set forth in claim 16, further including:
   biasing means for normally biasing the push rod sufficiently away from the far end portion of the tubular member to allow the distal end portion of the member to be held in the bore; and
   means for selectively overcoming the biasing means so as to expel the distal end portion of the member from the bore.

18. A combination of a ureteral stent as set forth in any one of claims 1, 2, or 3 and insertion means, wherein the insertion means comprises an elongated pusher bonded to the distal end portion of the member to form an assemblage.

19. A combination of ureteral stent and insertion means as set forth in claim 18, wherein the assemblage has an outer diameter substantially equal to the initial outer diameter of the member, the pusher being formulated of a dissolvable or biodegradable polymer which dissolves or biodegrades a selectable time following insertion of the assemblage into the ureter.

20. A combination of ureteral stent and insertion means as set forth in claim 18, wherein the assemblage has an outer diameter substantially equal to the initial outer diameter of the member, the assemblage further having a suture attached to and extending from the member, the suture being imbedded longitudinally along the pusher, the pusher being formulated of a dissolvable or biodegradable polymer which dissolves or biodegrades a selectable time following insertion of the assemblage into the ureter.

21. A combination of ureteral stent and insertion means as set forth in claim 19, wherein the dissolvable or biodegradable polymer is selected from the group consisting of the dissolvable polymers polyethylene oxides, polyvinylacetates, polyvinylpyrrolidones, polyethylene oxide based polyether urethanes and starch and cellulose derivatives, and of the biodegradable polymers polyorthoesters, polylactides, polyglycolides, copolymers thereof, collagen, polycaprolactones and polyglutonates.

22. A combination of ureteral stent and insertion means as set forth in claim 20, wherein the dissolvable or biodegradable polymer is selected from the group consisting of the dissolvable polymers polyethylene oxides, polyvinylacetates, polyvinylpyrrolidones, polyethylene oxide based polyether urethanes and starch and cellulose derivatives, and of the biodegradable polymers polyorthoesters, polylactides, polyglycolides, copolymers thereof, collagen, polycaprolactones and polyglutonates.

23. A ureteral stent as set forth in any one of claims 1, 2, and 3, wherein the member is tubular and defines a lumen which has internal ribs longitudinally along its length.

24. A ureteral stent comprising an elongated member having a proximal end portion and a distal end portion joined by a body portion, the elongated member having an initial member outer diameter and including retention means for retaining the stent within a ureter, the member being formulated of a physiologically acceptable polymer capable of hydrating with concurrent softening and with concurrent expanding from the initial member outer diameter to form an enlarged final member outer diameter, the polymer being formulated such that a selectable time following hydration the final member outer diameter reduces in situ to a smaller diameter.

25. A ureteral stent as set forth in claim 23, wherein the elongated member has an initial stiffness above about 100 Shore A and wherein upon hydration the initial stiffness of the distal end portion softens to a final softness which falls below 100 Shore A.

26. A ureteral stent as set forth in claim 24, wherein upon hydration the proximal end portion softens to about 70 Shore A to about 70 Shore D, and wherein upon hydration the distal end portion softens to about 30 to about 100 Shore A.

27. A ureteral stent as set forth in claim 24, wherein the polymer comprises a hydrophilic component capable of hydrating and the polymer upon hydration softens and expands the initial member outer diameter by from about 5% to about 300%.

28. A ureteral stent as set forth in claim 27, wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, starches, modified starches, alginates, hydroxy ethyl carbohydrates and mixtures and copolymers thereof.

29. A ureteral stent as set forth in claim 24, wherein the polymer comprises a hydrophilic component and a non-hydrophilic component in a selected ratio, the ratio of hydrophilic to non-hydrophilic component being selected such that upon hydration the polymer softens and expands the initial member outer diameter by from about 5% up to about 300%.

30. A ureteral stent as set forth in claim 29, wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, starches, modified starches, alginates, hydroxy ethyl carbohydrates and mixtures and copolymers thereof and the non-hydrophilic component is selected from the group consisting of silicone, an aliphatic polyurethane, an aromatic polyurethane, a polyether polyurethane, a polyester polyurethane, an ethylene copolymer, a polyamide, an aliphatic polyester or mixtures or copolymers thereof.

31. A ureteral stent as set forth in claim 24, wherein the retention means is formed upon hydration of the member.

32. A ureteral stent comprising an elongated member having a proximal end portion and a distal end portion joined by a body portion, the elongated member having an initial member outer diameter, the member being formulated of a physiologically acceptable polymer capable of hydrating with concurrent softening and with concurrent expanding from the initial member outer diameter to form a final member outer diameter, the polymer being formulated such that retention means for retaining the stent within a ureter forms upon hydration of the stent within the ureter.

33. A ureteral stent as set forth in claim 32, wherein the elongated member has an initial stiffness above about 100 Shore A and wherein upon hydration the initial stiffness of the distal end portion softens to a final softness which falls below 100 Shore A.

34. A ureteral stent as set forth in claim 32, wherein upon hydration the proximal end portion softens to about 70 Shore A to about 70 Shore D, and wherein upon hydration the distal end portion softens to about 30 to about 100 Shore A.

35. A ureteral stent as set forth in claim 32, wherein the polymer comprises a hydrophilic component capable of hydrating and the polymer upon hydration softens and expands the initial member outer diameter by from about 5% to about 300%.

36. A ureteral stent as set forth in claim 35, wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, starches, modified starches, alginates, hydroxy ethyl carbohydrates and mixtures and copolymers thereof.

37. A ureteral stent as set forth in claim 32, wherein the polymer comprises a hydrophilic component and a non-hydrophilic component in a selected ratio, the ratio of hydrophilic to non-hydrophilic component being selected such that upon hydration the polymer softens and expands the initial member outer diameter by from about 5% up to about 300%.

38. A ureteral stent as set forth in claim 37, wherein the hydrophilic component is selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, starches, modified starches, alginates, hydroxy ethyl carbohydrates and mixtures and copolymers thereof and the non-hydrophilic component is selected from the group consisting of silicone, an aliphatic polyurethane, an aromatic polyurethane, a polyether polyurethane, a polyester polyurethane, an ethylene copolymer, a polyamide, an aliphatic polyester or mixtures or copolymers thereof.

39. A ureteral stent as set forth in claim 32, wherein the retention means includes proximal retention means formed upon hydration of the proximal end portion.

40. A ureteral stent comprising an elongated member having a proximal end portion and a distal end portion joined by a body portion, the elongated member having an initial member outer diameter and including retention means for retaining the stent within a ureter, the member being formulated of an inner section surrounded by an outer layer, the inner section being formulated of a physiologically acceptable polymer capable of hydrating with concurrent softening and with concurrent expanding such that the initial member outer diameter expands to form an enlarged final member outer diameter, the outer layer being formulated such that a selectable time following hydration the outer layer degrades or dissolves such that the final member outer diameter reduces in situ to a smaller diameter.

* * * * *